United States Patent
Haggerty et al.

(10) Patent No.: US 11,664,109 B2
(45) Date of Patent: *May 30, 2023

(54) ACTIVITY MONITORING SYSTEMS AND METHODS

(71) Applicant: MEDTRONIC MINIMED, INC., Northridge, CA (US)

(72) Inventors: Matthew N. Haggerty, Minnetonka, MN (US); Erik R. Hoeg, Plymouth, MN (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/563,061

(22) Filed: Dec. 28, 2021

(65) Prior Publication Data

US 2022/0122713 A1 Apr. 21, 2022

Related U.S. Application Data

(63) Continuation of application No. 16/777,066, filed on Jan. 30, 2020, now Pat. No. 11,244,753.

(51) Int. Cl.
*G16H 20/60* (2018.01)
*G16H 40/67* (2018.01)
(Continued)

(52) U.S. Cl.
CPC ............ *G16H 20/60* (2018.01); *A61B 5/1112* (2013.01); *A61B 5/1118* (2013.01);
(Continued)

(58) Field of Classification Search
None
See application file for complete search history.

(56) References Cited

U.S. PATENT DOCUMENTS

| 4,755,173 A | 7/1988 | Konopka et al. |
| 5,391,250 A | 2/1995 | Cheney, II et al. |

(Continued)

FOREIGN PATENT DOCUMENTS

| WO | 2018164886 A1 | 9/2018 |
| WO | 2019157102 A1 | 8/2019 |
| WO | 2019183404 A1 | 9/2019 |

*Primary Examiner* — Kristy A Haupt (57) ABSTRACT

Activity monitoring systems and methods are disclosed. Systems include a continuous glucose monitoring device for a user including a glucose sensor for monitoring blood glucose levels of the user during an activity. An activity monitoring device is associated with the user and includes an activity sensor for tracking movement of the user during the activity. A display device is associable with the user during the activity. At least one processor is configured to execute program instructions configurable to cause the at least one processor to: receive activity data from the activity monitoring device; cause to be displayed at least some of the activity data on the display device; receive blood glucose data from the continuous glucose monitoring device; determine a product consumption recommendation based on the blood glucose data and the activity data, wherein the product consumption recommendation includes a recommendation of when the user should consume carbohydrates in order to maintain blood glucose levels within a specified target range during the activity; cause to be displayed the product consumption recommendation on the display device; and record an activity log including the activity data and the blood glucose data with respect to time.

20 Claims, 5 Drawing Sheets

(51) Int. Cl.
  *G16H 10/60* (2018.01)
  *G06N 20/00* (2019.01)
  *A61B 5/11* (2006.01)
  *A61B 5/145* (2006.01)
  *A61B 5/1477* (2006.01)
  *A61B 5/00* (2006.01)
  *G06K 7/10* (2006.01)
  *G06K 7/14* (2006.01)

(52) U.S. Cl.
  CPC ........ *A61B 5/1477* (2013.01); *A61B 5/14532* (2013.01); *A61B 5/681* (2013.01); *A61B 5/7264* (2013.01); *A61B 5/742* (2013.01); *G06K 7/10297* (2013.01); *G06K 7/10366* (2013.01); *G06K 7/10722* (2013.01); *G06K 7/1413* (2013.01); *G06K 7/1417* (2013.01); *G06N 20/00* (2019.01); *G16H 10/60* (2018.01); *G16H 40/67* (2018.01); *A61B 2562/0219* (2013.01)

(56) References Cited

U.S. PATENT DOCUMENTS

| | | |
|---|---|---|
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 11,244,753 B2 * | 2/2022 | Haggerty ............. A61B 5/1477 |
| 2003/0208113 A1 | 11/2003 | Mault et al. |
| 2007/0123819 A1 | 5/2007 | Mernoe et al. |
| 2010/0160861 A1 | 6/2010 | Causey, III et al. |
| 2017/0011184 A1 | 1/2017 | Ajayi et al. |
| 2019/0209777 A1 | 7/2019 | O'Connell et al. |
| 2021/0153787 A1 | 5/2021 | Parker et al. |

* cited by examiner

ACTIVITY MONITORING SYSTEMS AND METHODS

CROSS-REFERENCE TO RELATED APPLICATION(S)

This application is a continuation of U.S. patent application Ser. No. 16/777,066, filed Jan. 30, 2020, which is hereby incorporated by reference in its entirety for all purposes.

TECHNICAL FIELD

Embodiments of the subject matter described herein relate generally to systems and methods for monitoring activity of a user. More particularly, embodiments of the subject matter relate to systems and methods that monitor an analyte of a user, such as blood glucose, during an activity.

BACKGROUND

A variety of activity monitoring devices (or activity/fitness trackers) have been developed. An activity monitoring device is a device for monitoring and tracking fitness-related metrics during an activity such as walking, running, swimming, cycling, etc. Fitness related metrics include activity distance, such as distance walked, activity time, speed, elevation changes, estimated calories burned during the activity and heartbeat. Many activity monitoring devices are computers that are wearable or are able to be carried during the activity, such as with smartphones or smartwatches. Activity monitoring devices can include a multitude of activity sensors including GPS receivers, motion sensors such as accelerometers and gyroscopes, altimeters and heart rate monitors. Various software platforms, accessible through a smartphone, web browser, etc., are available for logging activity metrics so that a user can review a past exercise activity, such as a run, and so that the user can compare the activity metrics with the user's historical exercise activities.

To improve athletic performance during training or competitions, athletes may consume products containing carbohydrates, such as glucose. Example carbohydrate containing products include energy bars, energy gels, energy tablets and sports drinks. In order to provide energy quickly, most of the carbohydrates are various types of sugars like fructose, glucose, maltodextrin and others in various ratios, potentially combined with more complex carbohydrate sources. Today, athletes do not know exactly when and how much glucose to consume to achieve optimal performance while exercising. An athlete may rely on the carbohydrate packaging for guidance on how much and how often to consume a particular product. One known gel package advises that each energy gel includes 100 calories and that the whole contents of one packet should be consumed every 45 minutes.

The highly generic energy consumption guidance provided on energy products will often not be suitable for a particular athlete. Athletes will have different metabolic rates and thus consume energy at different rates. In addition, the calorie burn rate will differ between exercises and between athletes based on a variety of variable factors (hydration, intensity and duration of exercise, metabolic rate, etc.). Athletes would like to consume a sufficient amount of the carbohydrate containing products to meet their energy needs during exercise and yet do not want to overconsume energy products because of potential disagreement with the digestive system and other undesired factors.

Accordingly, it is desirable to provide activity monitoring systems and methods that are able to provide a user with more accurate guidance on when to consume a carbohydrate containing product, thereby potentially realizing enhanced athletic performance. In addition, it is desirable to systematically track consumption of carbohydrate containing products during exercise for subsequent analysis and optimization. Furthermore, other desirable features and characteristics will become apparent from the subsequent detailed description and the appended claims, taken in conjunction with the accompanying drawings and the foregoing technical field and background.

BRIEF SUMMARY

In one aspect, an activity monitoring system is provided. The system includes a continuous glucose monitoring device for a user, which includes a glucose sensor for monitoring blood glucose levels of the user during an activity. An activity monitoring device is associable with the user, the activity monitoring device comprising an activity sensor for tracking movement of the user during the activity. A display device is associable with the user during the activity. At least one processor is in operable communication with the continuous glucose monitoring device and the activity monitoring device. The at least one processor configured to execute program instructions. The program instructions are configurable to cause the at least one processor to: receive activity data from the activity monitoring device; cause to be displayed at least some of the activity data on the display device; receive blood glucose data from the continuous glucose monitoring device; determine a product consumption recommendation based on the blood glucose data and the activity data, wherein the product consumption recommendation includes a recommendation of when the user should consume carbohydrates in order to maintain blood glucose levels within a specified target range during the activity; cause to be displayed the product consumption recommendation on the display device; and record an activity log including the activity data and the blood glucose data with respect to time.

In embodiments, the activity sensor includes a Global Positioning System, GPS, receiver. In embodiments, the activity sensor includes at least one of an accelerometer and an altimeter. In embodiments, the activity data includes at least one of distance, elevation and steps.

In embodiments, the activity monitoring system includes a user interface. The program instructions are configurable to cause the at least one processor to: receive product data, via the user interface, regarding a carbohydrate containing, product; and record the activity data, the blood glucose data and the product data with respect to time in the activity log. In embodiments, the user interface includes a product reader configured to read the product data from a package of the carbohydrate containing product. In embodiments, the product reader includes at least one of an optical reader and a wireless communications reader.

In embodiments, the program instructions are configured to cause the at least one processor to determine a downward trend in the blood glucose data and to determine the product consumption recommendation based on the downward trend in the blood glucose data.

In embodiments, the program instructions are configured to cause the at least one processor to determine a product consumption recommendation based on the blood glucose data. The product consumption recommendation includes a recommendation of when the user should consume a carbohydrate containing product and which carbohydrate containing product, from a plurality of carbohydrate containing products, the user should consume in order to maintain desirable blood glucose levels within a specified target range during the activity.

In embodiments, the program instructions are configured to cause the at least one processor to analyze historical activity logs including activity data, blood glucose data and product data with respect to time in order to generate one or more blood glucose response parameters, wherein the one or more blood glucose response parameters represent a user's blood glucose response to consuming one or more carbohydrate containing products, and wherein the program instructions are configured to cause the at least one processor to determine a product consumption recommendation based on the glucose data, the activity data and the one or more blood glucose response parameters. In embodiments, the one or more blood glucose response parameters include at least one of a blood glucose change parameter, a blood glucose rate of change parameter, and a blood glucose change time delay parameter.

In embodiments, the activity monitoring device is a wrist wearable device or a smart phone paired with the continuous glucose monitor.

In embodiments, the glucose sensor includes a sensor electrode for subcutaneous placement.

In another aspect, a method of monitoring an activity is provided. The method includes: receiving, by at least one processor, activity data from an activity monitoring device for tracking movement of a user during an activity; displaying, by the at least one processor, at least some of the activity data on a display device associated with the user during the activity; receiving, by the at least one processor, blood glucose data from a continuous glucose monitoring device worn by the user during the activity; determining, by the at least one processor, a product consumption recommendation based on the blood glucose data, wherein the product consumption recommendation includes a recommendation of when the user should consume a carbohydrate containing product in order to maintain blood glucose levels within a specified target range during the activity; displaying, by the at least one processor, the product consumption recommendation on the display device during the activity; and recording, by the at least one processor, an activity log including the activity data and the blood glucose data with respect to time.

In embodiments, the activity is a form of physical exercise including walking, running or cycling.

In embodiments, the method includes reading product data from a package of a carbohydrate containing product during the activity using an optical reader or a wireless communications reader; receiving, by the at least one processor, the product data; and recording, by the at least one processor, the activity data, the blood glucose data and the product data in the activity log with respect to time.

In embodiments, the method includes analyzing one or more historical activity logs including activity data, blood glucose data and product data using a machine learning algorithm to determine user response parameters, wherein the user response parameters represent a user's blood glucose response to consuming different carbohydrate containing products during an activity.

In embodiments, the method includes determining, by the at least one processor, the product consumption recommendation based on the blood glucose data and the user blood glucose response parameters, wherein the product consumption recommendation includes a recommendation of when the user should consume a carbohydrate containing product and which of the different carbohydrate containing products the user should consume in order to maintain blood glucose levels within a specified target range during the activity.

In embodiments, the activity monitoring device is a wrist wearable device.

In another aspect, a non-transitory computer-readable storage medium having program instructions for monitoring an activity is provided. The program instructions are configurable to cause at least one processor to: receive activity data from an activity monitoring device associated with a user during an activity; displaying at least some of the activity data on a display device associated with the user during the activity; receive blood glucose data from a continuous glucose monitoring device worn by the user during the activity; determine a product consumption recommendation based on the blood glucose data, wherein the product consumption recommendation includes a recommendation of when the user should consume a carbohydrate containing product and a quantity of carbohydrate containing product that the user should consume in order to maintain blood glucose levels within a specified target range during the activity; display the product consumption recommendation on the display device during the activity; and record an activity log including the activity data and the blood glucose data with respect to time.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or instructions that perform the various tasks. In certain embodiments, the program or code segments are stored in a tangible processor-readable medium, which may include any medium that can store or transfer information. Examples of a non-transitory and processor-readable medium include an electronic circuit, a semiconductor memory device, a ROM, a flash memory, an erasable ROM (EROM), a floppy diskette, a CD-ROM, an optical disk, a hard disk, or the like.

For the sake of brevity, conventional techniques related to signal processing, data transmission, signaling, network control, and other functional aspects of the systems (and the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in an embodiment of the subject matter.

Figure 1:
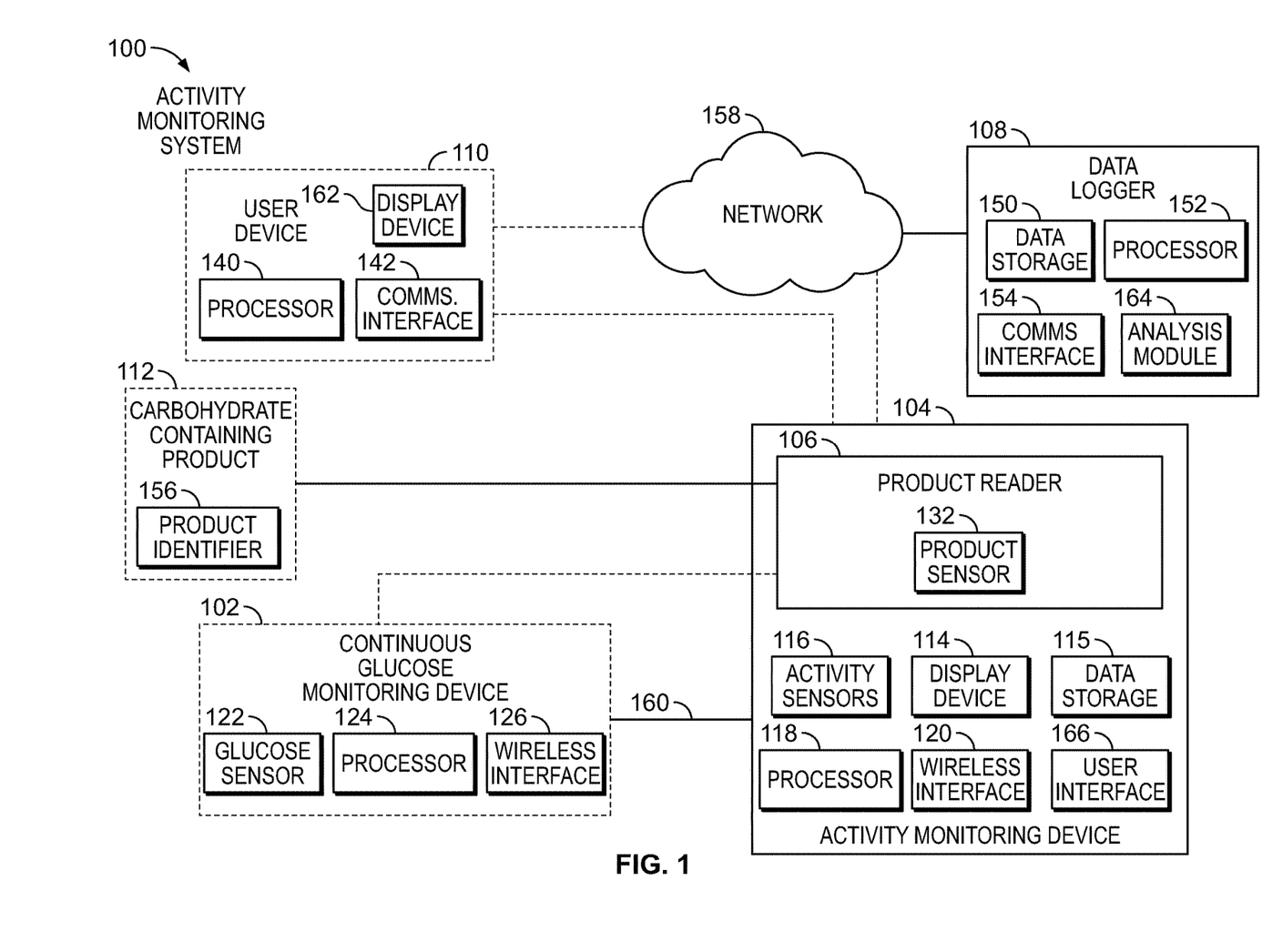
FIG. 1 is a block diagram of a system for activity monitoring, in accordance with various embodiments.

FIG. 1 is a block diagram of an activity monitoring system 100, in accordance with an embodiment. Activity monitoring system 100 includes a continuous glucose monitoring device 102, an activity monitoring device 104, a product reader 106, a data logger 108, a user device 110 and a carbohydrate containing product 112. Continuous glucose monitoring device 102 is configured to be worn by a user for monitoring blood glucose levels of the user during an activity. Activity monitoring device 104 is associated with (e.g. worn by, carried by or otherwise physically associated with) the user for tracking movement of the user during the activity. Continuous glucose monitoring device 102 is configured to output blood glucose data representative of the concentration of glucose present in the blood of the user, which is subject to continuous variation during the activity. Activity monitoring device 104 is configured to output activity data providing an activity metric associated with the user's movement during the activity or exercise. Exemplary metrics include distance moved, speed, heart rate, step count, cadence, elevation change, activity time, elevation change rate, power, energy output, etc.

In the exemplary embodiment, a display device 114 is included as part of the activity monitoring device 104, although they do not need to be part of the same device in other embodiments. Activity monitoring system 100 has access to computer processing power in the form of one or more processors 118, 124, 140, 152. One or more of processors 118, 124, 140, 152 are configured to execute computer program instructions to determine a product consumption recommendation based on blood glucose data from the continuous glucose monitoring device 102. The product consumption recommendation refers to a recommendation of when the user should consume carbohydrates in order to maintain blood glucose levels within a specified target range during the activity and optionally also which carbohydrate containing product 112 should be consumed by the user. The product consumption recommendation may identify which carbohydrate containing product to identify by including a product type identification, a brand identification, a carbohydrate amount recommendation and/or a calorie amount recommendation. Display device 114 is configured to display at least some of the activity data (e.g. one or more activity metrics such as distance moved, speed, time and/or heart rate) and to display the product consumption recommendation (e.g. so that the display device 114 simultaneously shows the activity data and the product consumption recommendation or so that the product consumption recommendation temporarily replaces the activity data). Activity monitoring system 100 is further configured to record an activity log including the activity data and the blood glucose data with respect to time. The activity log may be recorded in data storage 115 of the activity monitoring device 104 and/or some other data storage such as data storage 150 of data logger 108.

Activity monitoring system 100 allows accurate timing of when a user should consumer a carbohydrate containing product 112 based on real-time blood glucose data obtained during the activity. In this way, the user maintains optimal blood sugar levels during the activity in order to sustain energy output, whilst also ensuring that carbohydrate containing products are not overconsumed. Further, a data log is kept of blood glucose data and activity data allowing manual or automated analysis of the impact of the activity on blood glucose levels to assist learning on when, and how much, carbohydrate containing products should be consumed during exercise.

Product reader 106 includes a user interface in the form of a product sensor 132, in the present embodiment. Program instructions executable by the one or more of processors 118, 124, 140, 152 are configured to receive product data from product sensor 106 regarding a carbohydrate containing product 112. In embodiments, product sensor 132 is configured to read product data from a package of carbohydrate containing product 112. Product data can be a product identifier 156 allowing, optionally, product nutritional information (e.g. energy content, carbohydrate content, sugar content of carbohydrates, etc.) to be retrieved from local storage (e.g. from data storage 115) or from remote data storage. Alternatively, nutritional information can be read from packaging of carbohydrate containing product 112. Program instructions are configured to record activity data, blood glucose data and product data with respect to time in the activity log, thereby facilitating analysis of blood glucose response to carbohydrate containing products beings consumed during a particular activity. Such data enables manual or machine learning to be performed to assist activity monitoring system 100 in outputting future product recommendations (e.g. product recommendations as to when and optionally which product should be consumed based on prevailing blood glucose values, a desired blood glucose response and carbohydrate containing product consumption that will meet the desired blood glucose response). In some embodiments, product reader 106 includes at least one of an optical reader and a wireless communications reader as the product sensor 132, which will allow product data to be read and recorded during an activity (e.g. whilst running or cycling) with minimal disruption to the activity.

Figure 2:
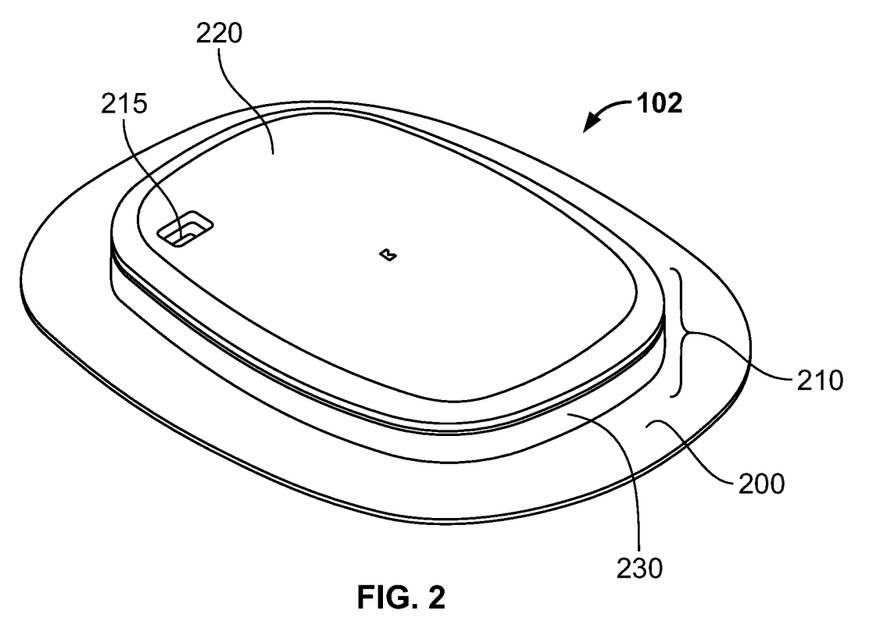
FIG. 2 is a perspective view of an exemplary continuous glucose monitoring device for use with the activity monitoring system of FIG. 1.
Figure 3:
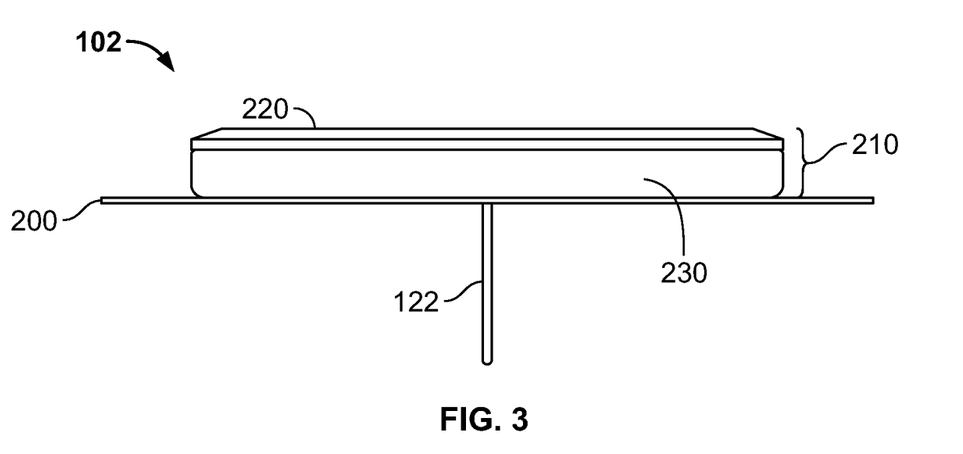
FIG. 3 is a side view of the continuous glucose monitoring device shown in FIG. 2.

An exemplary continuous glucose monitoring device 102 is shown in FIGS. 2 and 3, in accordance with an exemplary embodiment. Continuous glucose monitoring device 102 is a single-use, disposable device or a reusable disposable device or includes part disposable and part reusable components. Continuous glucose monitoring device 102 is configured to wirelessly connect with activity monitoring device 104 and/or with another user device 110 such as a mobile user device like a smartphone. Continuous glucose monitoring device 122 includes a glucose sensor 122, which may be a subcutaneous glucose sensor, a processor 124, and wireless interface 126. Processor 124 is configured to execute computer program instructions in order to obtain digitized glucose values based on blood glucose readings from glucose sensor 122 at predetermined sampling intervals and to wirelessly transmit continuous blood glucose values through wireless interface 126 to activity monitoring device 104 or user device 110. Continuous blood glucose values may be transmitted at the same rate as they are received, or a buffered approach may be taken so that bulk continuous blood glucose values are transmitted at a lesser rate than the predetermined sampling rate. Continuous glucose monitoring device 102 is configured to be worn on, e.g. applied to, the user (such as the skin of the user) during the activity.

Turning to FIGS. 2 and 3, a configuration of a continuous glucose monitoring device 102 includes a housing 210 including, in one example embodiment, an upper housing 220 with an upper major wall inside the upper housing, and a lower housing 230 with a lower major wall inside the lower housing 230, where the upper and lower major walls oppose each other. The housing 210 is shown as generally rectangular, but other shapes, such as square shapes, circular shapes, polygon shapes, can be used according to the size of the components housed inside and to increase comfort levels on the skin. The housing has a low profile to decrease visibility through clothing and also to decrease discomfort and interference from the sensing device when it is worn on a patient's skin.

The housing 210 is attached to an adhesive patch 200 for press-on adhesive mounting onto the user's skin. The patch may be sized such that it has as much adhesion to skin as possible while not being too large for comfort or to easily fit on a user. The adhesive patch may be made out of a material with stretch to increase comfort and to reduce failures due to sheer. It is understood that alternative methods or techniques for attaching the housing 210 to the skin of a patient, other than an adhesive patch, also may be contemplated. The housing 210 may be made out of a suitable rigid plastic that can safely and securely hold electrical components of the sensor. Suitable plastic materials include, as an example and in no way by limitation, ABS, nylon, an ABS/PC blend, PVC, polytetrafluoroethylene (PTFE), polypropylene, polyether ether ketone (PEEK), or the like, and polycarbonate. In this configuration, the upper housing 220 includes a small opening 215 for pass through of a battery pull tab (not shown) used to block the battery from contacting the electronic battery contacts prior to use, thus preventing battery depletion.

The adhesive patch 200 may be bonded to the lower housing 230 along the entire footprint of the lower housing 230, or over just a portion, such as the perimeter of the housing 210. Shear, tensile, peel, and torque loads are distributed as much as possible. The patch 200 may be ultrasonically welded to the lower housing 230 or adhered, for example, by a double-sided adhesive. In configurations, the adhesive patch extends further than the edge of the lower housing 230.

FIG. 3 shows a side view of the continuous glucose monitoring device 202 with thin film glucose sensor 122 extending out of the housing 210 through the patch 200, which may include a hole for the glucose sensor 122 to pass through. The low profile/height of the housing 210 can be seen in FIG. 3. As shown in FIG. 3, the flexible thin glucose sensor 122 comprises a relatively thin and elongated element which can be constructed according to so-called thin mask techniques to include elongated conductive elements embedded or encased between layers of a selected insulative sheet material such as polyimide film or sheet. Support may be provided to the flexible thin sensor. For example, the flexible thin sensor may be contained in a flexible tube to provide support. However, it is possible for a thicker glucose sensor 122 to be stiff enough to reduce instances of sensor kinks without a flexible tube. A proximal end or head (not shown) of the glucose sensor 122 is relatively enlarged and defines electrical contacts (not shown) for electrical connection to a printed circuit board assembly (not shown) containing and connected to various electrical components of the continuous glucose monitoring device 102. An opposite or distal segment of the glucose sensor 122 includes a plurality of exposed sensor electrodes (not shown) for contacting patient body fluid when the sensor distal segment is placed into the body of the patient. The sensor electrodes generate electrical signals representative of blood glucose, wherein these signals are transmitted to internal sensor electronics (including processor 124 and wireless interface 126) and subsequently, via wireless interface 126, to activity monitoring device 104 and/or user device 110 for recordation and/or display of synchronously tracked activity data and blood glucose data. Further description of flexible thin film sensors of this general type may be found in U.S. Pat. No. 5,391,250, which is herein incorporated by reference. Sensor electronics including wireless transmitters of wireless interface 126 are discussed, for example, in U.S. Pat. No. 7,602,310, which is herein incorporated by reference.

The exemplary form of continuous glucose monitoring device 102 should, in no way, be considered limiting. Any of a variety of available continuous glucose monitoring device may be used in activity monitoring system 100 including separable sensor (re-usable a limited number of times) and transmitter (re-usable with more than one sensor) systems like those included in the Guardian™ Connect system or the MINIMED™ 630/670G systems.

Activity monitoring device 104 includes activity sensors 116, a display device 114, data storage 115, a processor 118 and a wireless interface 120. Various functions described herein relating to activity monitoring device 104 are performed by computer program instructions being executed on processor 118. Activity monitoring device 104 is configured to establish a wireless communications channel 160 with continuous glucose monitoring device 102 through wireless interface 126 of continuous glucose monitoring device 102 and wireless interface 120 of activity monitoring device 104. Activity monitoring device 104 is configured to receive blood glucose data from continuous glucose monitoring device 102 over wireless communications channel 160 and to receive activity data from activity sensors 116. Activity monitoring device 114 is configured to generate a display on display device 114 based on the activity data and the continuous glucose data. For example, real-time blood glucose values can be displayed on display device 114 in addition to activity metrics (such as speed, time, distance, heart rate, elevation, etc.). Further, an activity log can be kept in data storage 115, which logs, with respect to time, activity data and blood glucose data.

Activity monitoring device 104 is configured to establish the communications channel 160 with continuous glucose monitoring device through a pairing procedure, in some embodiments. The form of communication between activity monitoring device 104 and continuous glucose monitoring device 102 is not particularly limited. In embodiments, any low energy usage, radiofrequency data communication method can be used including Bluetooth, Zigbee, Wi-Fi HaLow, Z-wave, etc.

Activity sensors 116 include any combination of a GPS (Global Positioning System) receiver, at least one motion sensor such as accelerometers and gyroscopes, an altimeter and a heart rate monitor. Additional or alternative activity sensors can be included. A GPS receiver includes antennas that use a satellite-based navigation system with a network of satellites in orbit around the earth to provide position data. From position data, movement of a user during an activity can be sufficiently accurately tracked to allow distance moved during running, walking, cycling, swimming, etc. to be measured. Further, speed and time data for the activity is derivable from the GPS position data. An altimeter measures atmospheric pressure and derives height above sea level (or some other reference plane) based thereon. In alternative embodiments, elevation data is derived from the GPS position data or elevation data is derived from a combination of the GPS position data and measurements from the altimeter. Motion sensors such as multi-axis accelerometers and gyroscopes allow activity monitoring device 104 to differentiate types of activities and also to count steps during walking and running (cadence data), amongst other functions. Further, lap counts during swimming are facilitated by motion sensor by allowing a lap turn to be detected. One exemplary type of heart rate sensor is an optical heart rate sensor configured to direct light against the skin and to detect changes of reflectivity with heart beats. ECG type heart rate sensors are another possibility for measuring heart rate. Activity sensors 116 are configured to output, at a predetermined rate, a vector of activity data from the various sensors for subsequent processing by processor 118. Various processing steps can be performed by processor 118 on the vector of activity data including smoothing and de-noising pre-processing functions and further processing in order to obtain user understandable activity metrics in units selected by the user (e.g. speed in meters per second, kilometers per hour or miles per hour).

Activity monitoring device 104 is configured to receive blood glucose data during an activity and to determine a product consumption recommendation based on the blood glucose data. In accordance with various embodiments, activity monitoring device 104 is configured to compare blood glucose data, or a time derivative thereof, with a low blood glucose threshold corresponding to a blood glucose target range during the activity. The low blood glucose threshold can be predetermined or can be a dynamic parameter that is varied with learning about a user's blood glucose response to the activity based on historical activity and blood glucose data, as discussed further herein. The product consumption recommendation can be determined based on absolute blood glucose values dropping below a threshold value, based on a downward change in blood glucose over a preset time period being greater than a threshold vale, a negative rate of change of blood glucose value surpassing a threshold value and any combination thereof.

In some embodiments, activity monitoring device 104 is configured to monitor downward trend in blood glucose data in order to determine when a carbohydrate containing product 112 is to be consumed based on projecting when, in the future, blood glucose values will satisfy one or more thresholds. The projection may be based on the current activity (known from a setting of activity monitoring device 104 or from output of activity sensors 116) and the user's historical blood glucose response to the activity, as described in further detail below. In this way, the product consumption recommendation can indicate when in the future a carbohydrate containing product 112 should be consumed. In further embodiments, the blood glucose data, or a projection thereof, allows a type of carbohydrate containing product 112 to be determined as part of the product consumption recommendation. A desired blood glucose response to consuming a carbohydrate containing product 112 can be determined based on blood glucose data (and optionally from historical data concerning a user's blood glucose response to the current activity). Data on a blood glucose response, which may be user specific from historical blood glucose data, to a plurality of different carbohydrate containing products allows the activity monitoring device 104 to select which carbohydrate containing product 112 matches the desired blood glucose response. As such, the product consumption recommendation may include when a carbohydrate containing product 112 should be consumed and which carbohydrate containing product should be consumed (or at least an indication of a number of calories or a quantity and/or type of carbohydrates that should be consumed). In embodiments, the product consumption recommendation is determined based on blood glucose data received from the continuous glucose monitoring device 102 and activity data received from the activity monitoring device 104. In one example, type of activity (and optionally strenuousness) will impact rate of decrease in blood sugar, whilst blood glucose data will provide reference information. Activity and blood glucose data will enhance prediction on likely blood glucose response to current activity and thus when a product should be consumed and what type of product (in terms of correcting blood glucose response drop) is recommended to be consumed. In some examples described herein, a blood glucose response prediction is determined from algorithmic learnings from historical activity and blood glucose data, thereby allowing even better timing and information content for product consumption recommendations.

In examples, activity monitoring device 104 is configured to provide differing product consumption recommendations depending on varying activity data and vary blood glucose data. Walking and cycling are slower burn activities than fast jogging, for example. Thus, activity monitoring device 104 is configured to output a product consumption recommendation at a more urgent timing than for faster calorie burning activities. However, total calorie usage may be higher for a particular user's typical cycling activities than for the user's typical running activities. Thus, a product type may be indicated by the product consumption recommendation having large total calorie content or slower blood glucose impact for some activities than others. By taking into account both activity data and blood glucose data, activity monitoring device 104 is configured to provide improved product consumption recommendations in terms of timing and what product to consume. In further embodiments, the product consumption recommendations are generated using learnings (e.g. blood glucose response parameters) that are user specific from historical blood glucose and activity data.

Figure 4:
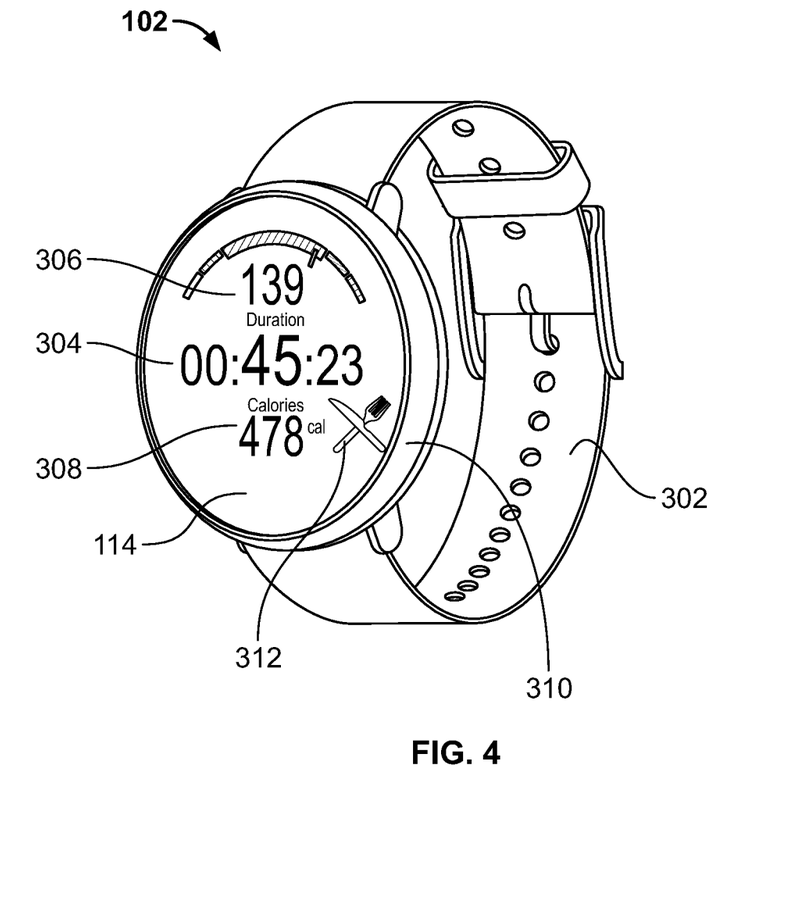
FIG. 4 is an exemplary display for an activity monitoring device of the activity monitoring system of FIG. 1, in accordance with various embodiments.

With reference to FIG. 4, an exemplary activity monitoring device 104 is illustrated. Activity monitoring device 104 is, in the present embodiment, a wrist wearable device. However, activity monitoring device 104 may be a smart phone or other device having the components and functions of the activity monitoring device 104 described with reference to FIG. 1. In the embodiment of FIG. 4, activity monitoring device 104 includes a wrist strap 302 connected to a housing 310 upon which the display device 114 is mounted so that the display device 114 is worn against the wrist of a user. Activity sensors 116, data storage 115 and processor 118 are located within housing 310. Other embodiments are envisaged than a wrist wearable device such as activity monitoring device 104 being at least partly mountable on a bicycle frame (e.g. at least display device 114 is mounted to handle bars).

In accordance with embodiments, display device 114 is configured, through processor 118 and program instructions, to display the product consumption recommendation and activity metrics derived from activity data obtained through activity sensors 116. One example display is shown in FIG. 4, which displays three activity metrics on one screen. In a first area 306 of the screen, current heart rate is displayed (along with an optional graphic differentiating heart rate zones). In a second area 304 of the screen, activity time is displayed. In a third area 308, energy consumed (in calories) during activity is displayed. These activity metrics are derived from activity data obtained from activity sensors 116. Any combination of activity metrics can be displayed (e.g. any one, two, three or more of speed, heart rate, energy consumed, power, altitude, time, slope, rate of change of elevation, etc) and the configuration of the display screen can be user selectable. Different numbers of areas for displaying activity metrics can be utilized such as 1, 2 or 4. In some embodiments, one of the areas 304, 306, 308 is used to display current blood glucose values based on blood glucose data from continuous glucose monitor 102. In embodiments, trend of blood glucose values is also displayed such as through the use of a downward arrow for decreasing blood sugar trend and upward arrow for increasing blood sugar trend. Differing angles of down and up arrows may also be used to indicate differing rates of decrease or increase in blood glucose values.

With continued reference to FIG. 4, the display includes a notification 312 concerning the product consumption recommendation, in one example embodiment. In one example, notification 312 appears when a carbohydrate containing product 112 should be consumed. Notification 312 may be a simple indication conveying that consumption of a carbohydrate containing product 112 is recommended (e.g. a display of a knife and fork icon). In another example, notification 312 conveys a future time when the carbohydrate containing product 112 should be consumed (such as via a countdown timer or an absolute time display). In some embodiments, notification 312 conveys not only when the carbohydrate containing product 112 should be consumed, but also which carbohydrate containing product 112 should be consumed, e.g. via a graphic representing a particular brand or type of carbohydrate containing product 112 (e.g. an energy bar icon, a gel pack icon, an energy drink icon, etc.) or a number of calories that should be consumed. The information on which carbohydrate containing product 112 is recommended is included in the processor determined product consumption recommendation, as described further herein. In yet further examples, the icon is user selectable (e.g. via a touch screen feature of display device 114) to show further details of the product consumption recommendation such as when and what to consume. In the embodiment of FIG. 4, the product consumption recommendation (or at least part of it) is displayed in the notification 312 on the same screen as one or more areas 304, 306, 308 of the screen displaying activity data. In alternative executions, the product consumption recommendation is displayed on a separate screen that temporarily replaces the screen showing activity data. The temporary display of the product consumption recommendation screen can be for a predetermined time, until a user selects to revert to the activity data screen and/or until detection has been made, via product reader 106, of a carbohydrate containing product 112 being consumed.

In accordance with various embodiments, activity monitoring system 100 includes a product reader 106 having a product sensor 132 configured to read product data from a package of the carbohydrate containing product 112. The package of the carbohydrate containing product 112 includes a sensor readable product identifier 156 and the product reader 106 is configured to read the product identifier 156. In some embodiments, the product sensor 132 is an optical reader. For example, a camera could be used as the product sensor 132 and recognition software could be included in the product reader 106. Recognition software is provided as program instructions executed by processor 118, 124 of continuous glucose monitoring device 102 or activity monitoring device 104. In some embodiments, the recognition software is configured to recognize branding of the package as the product identifier 156. In additional or alternative embodiments, the recognition software is configured to perform optical character recognition to identify alphanumeric characters on the packaging (e.g. brand name, product weight and/or Global Trade Identification Number (GTIN), etc). In other embodiments, the camera and recognition software is configured to decode a QR code, barcode or other graphical (non-alphanumeric) coded product identifier 156. In some embodiments, the product reader 106 includes a wireless communications reader as the product sensor 132. Carbohydrate containing product 112 includes a passive tag encoding the product identifier 156. The passive tag is able to be interrogated by electromagnetic (e.g. radiofrequency) energy from the product sensor 132 such that the product reader 106 is able to retrieve the product identifier 156. In examples, the passive tag is a Radio Frequency Identification (RFID) tag or a Near Field Communication (NFC) tag. Although, product reader 106 has been described as reading product identifier 156, other product data could be read including nutritional data such as energy and carbohydrate nutritional data. Alternatively, if such nutritional data is required, nutritional data corresponding to the product identifier 156 could be derived by looking it up from remote or local data storage.

Product reader 106 is shown in the block diagram of FIG. 1 as being part of activity monitoring device 104. In other embodiments, product reader 106 is included as part of continuous glucose monitoring device 102 or as a separate device. In embodiments, product reader 106 is included within housing 310 of activity monitoring device 104 or within a housing of continuous glucose monitoring device 102. Alternatively, product reader 106 may be included in a separated housing (that is worn by the user or otherwise physically associated with the user during an activity). During an activity, a user may view a product consumption recommendation on display device 114 of activity monitoring device 104. The user would take a carbohydrate containing product 112 (e.g. from a clothing pocket) and tap the carbohydrate containing product 112 against the product reader 106 (e.g. against the activity monitoring device 104 or the continuous glucose monitoring device 102) or otherwise have the product identifier 156 read during the activity (without significantly interrupting the activity). Product reader 106 is configured to be in electronic communication with activity monitoring device, optionally via continuous glucose monitoring device 112. As such, activity monitoring device 104 is configured, via computer program instructions, to receive the product identifier 156 or other product data and to store the product data in activity log in data storage 115. Like activity data and blood glucose data, product data is associated with a timestamp in activity log so that time of consumption of a carbohydrate containing product 112 can be tracked in addition to identification of the carbohydrate containing product 112. In some embodiments, activity log is provided as XML, data such as including activity data formats TCX or GPX.

Activity monitoring system 100 is shown to include product reader 106 in the embodiment of FIG. 1. However, other embodiments could be provided without a product reader 106 such that product data is not tracked or such that different data entry methods are utilized. For example, continuous glucose monitoring device 102 or activity monitoring device 104 could include another user interface 166, such as buttons and/or touchscreen display device 114, to allow a user to select, during the activity, consumption of a carbohydrate containing product 112 and which carbohydrate containing product 112 has been consumed. For example, activity monitoring device 104 can be loaded with a user selectable list of different carbohydrate containing products and the list may be configurable by user interaction through user interface 166. In this way, the user can select a carbohydrate containing product using activity monitoring device 104 as it is consumed during the activity. Although manual data entry is more disruptive to the activity than use of product reader 106, this convenience cost may be offset in some implementations by reduced hardware requirements.

In the exemplary embodiment of FIG. 1, activity monitoring system 100 includes a user device 110. User device 110 includes a processor 140 and communications interface 142. User device 110 is configured to be in communication with activity monitoring device 104 and data logger 108 so as to facilitate sending activity log from activity monitoring device 104 to remote data logger 108 over network 158 when activity monitoring device 104 is not internet capable. In other embodiments, activity monitoring device 104 is configured to send activity logs to data logger 108 directly, rather than via user device 110, and thus is provided with internet communication capability. Accordingly, user device 110 is an optional component of activity monitoring system 100. User device 110 may be a smartphone, a tablet device, a desktop computer, a laptop or other personal computing device. Although only one user device 110 is illustrated, more than one user device performing the functions described herein is envisaged such as a smartphone and another personal electronic device (e.g. a laptop).

In one embodiment, user device 110 is configured to communicate with activity monitoring device 104 after a pairing procedure to establish a wireless communications channel. User device 110 and activity monitoring device 104 are configured to communicate by Bluetooth, Zigbee, Wi-Fi HaLow, Z-wave or other short-range, low energy wireless communications scheme. In other embodiments, activity monitoring system 100 includes a wired connection between user device 110 and activity monitoring device 104 for communication of activity log therebetween. In one specific example, user device 110 is a smartphone or tablet, continuous glucose monitoring device 102 is configured to be applied to the skin (e.g. in the abdomen area) and activity monitoring device 104 is a wrist wearable device. Activity data, blood glucose data and product data are collected in activity log stored in data storage 115 of activity monitoring device 104 for communication with user device 110 over, for example, a Bluetooth connection. Activity log is uploaded by user device 110 to data logger 108.

Activity monitoring system 100 includes data logger 108. Data logger 108 includes data storage 150, processor 152 and communications interface 154. Processor 154 of data logger 108 is configured to execute computer program instructions to perform the various functions of the data logger 108 described herein. Data logger 108 is configured to receive activity logs from activity monitoring device 104 over network 158 through communications interface 154. In embodiments, activity logs stored by data logger 108 include activity data, blood glucose data and product data that are timestamped to allow charts to be displayed in which activity data (of all kinds of metrics such as speed, elevation, heart rate, etc.), blood glucose data and product data are constructed with respect to the same time axis or with respect to more than one time axis for respective charts that share the same time scale. Data logger 108 is configured to record activity logs in data storage 150. Data logger 108 is a cloud platform that is accessible by users via an internet connection and over network 158, in accordance with various embodiments. In embodiments, data logger 108 is configured to store, in data storage 150, historical activity logs in association with a user profile. A user profile is accessible by a secure sign in process, generally requiring a password and username authentication process. In some embodiments, data logger 108 is configured as a social networking platform in which users can connect with each other in order to view and compare with other user's activities in their network. In accordance with various embodiments, a user profile in data logger 108 is accessible by a user from user device 110 and/or from activity monitoring device 104.

Figure 5:
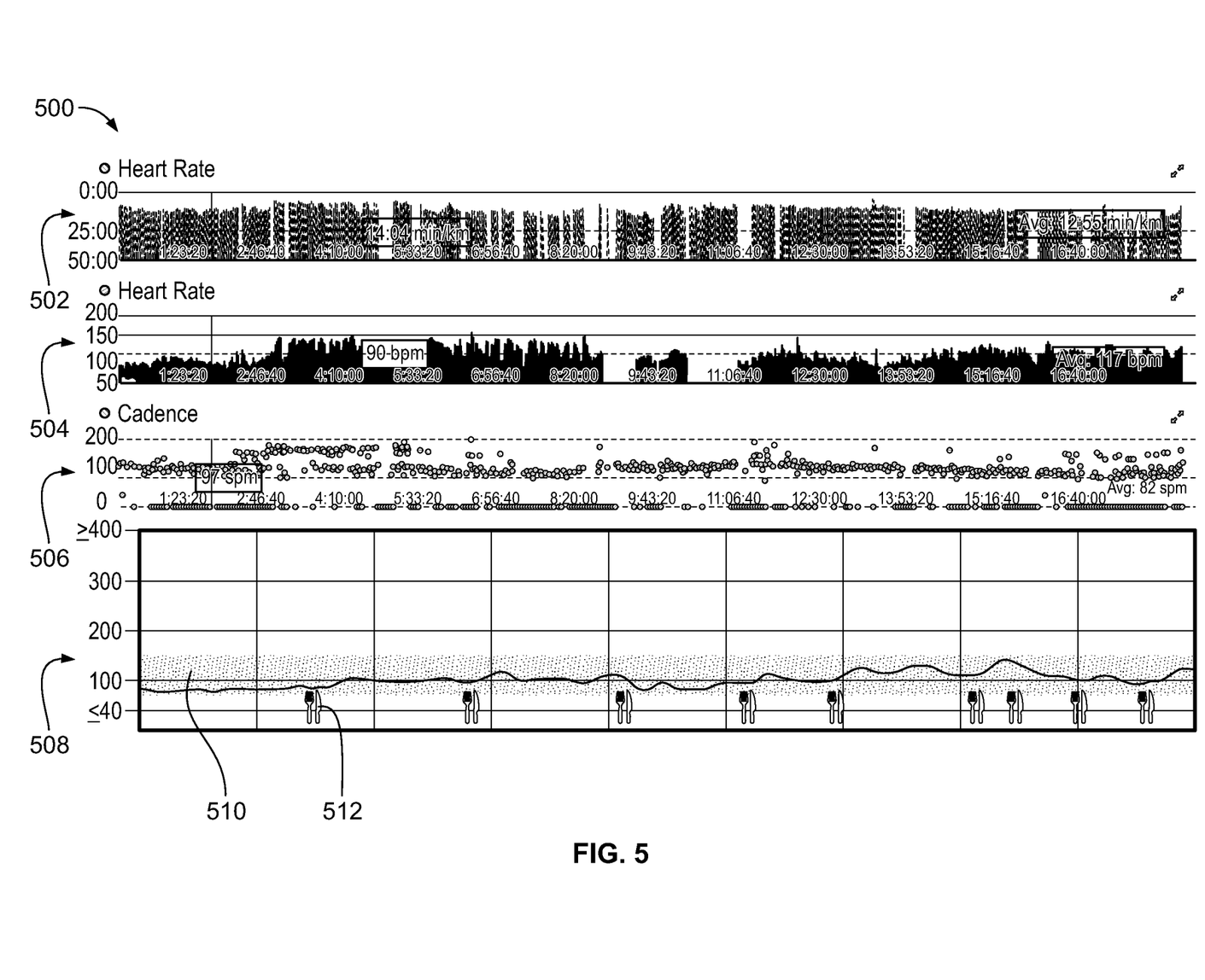
FIG. 5 is an exemplary activity report obtained from a data logger of the activity monitoring system of FIG. 1, in accordance with various embodiments.

In accordance with various embodiments, user device 110 and/or activity monitoring device 104 is configured to display, on respective display devices 114, 162, one or more activity logs accessed through data logger 108. An activity log display 500 is shown in FIG. 5, which shows one example activity report displayed on display device 162 of user device 110 or display device 114 of activity monitoring device 104. Display 500 includes plural charts 502, 504, 506, 508 of a particular activity including one or more charts 502, 504, 506 of activity metrics and one or more charts 508 of blood glucose data and product data. The plural charts 502, 504, 506, 508 may be displayed to share the same time axis or may be displayed to share a same scale time axis, thereby facilitating analysis. In the exemplary embodiment, chart 502 is a chart of pace (minutes per kilometer) against time, chart 504 is a chart of heart rate (beats per minute) against time and chart 506 is a chart of cadence (steps per minute) against time. Less or more activity metric charts could be provided in other embodiments. Further, different activity metrics could be displayed such as a chart of distance against time, elevation against time, energy consumed (calories) against time, etc. In the exemplary embodiment, chart 508 is a chart of blood glucose values (milligrams per deciliter) against time that additionally includes product data in the form of graphical elements 512. Graphical elements 512 indicate when a carbohydrate containing product had been consumed during the activity. Graphical element 512 may also indicate which kind of product had been consumed (based on product identifier included in product data) and optionally associated nutritional information (based on information extracted from product packaging or based on remote or local data look-up as described elsewhere herein). In examples, graphical element 512 may be selectable to provide further product data such as product identifier (e.g. brand name) and nutritional information (such as calorific content, weight, carbohydrate content, etc.).

In accordance with various embodiments described herein, one or more processors 118, 124, 140, 152 of activity monitoring system 100 are configured to analyze historical activity logs stored in data storage 150 of data logger. The historical activity logs include activity data, blood glucose data and product data with respect to time in order to generate one or more blood glucose response parameters. The one or more blood glucose response parameters represent a user's blood glucose response to consuming one or more carbohydrate containing products. In embodiments, the analysis of historical activity logs is performed by processor and computer programming of continuous glucose monitoring device 102, activity monitoring device 104, user device 110, data logger 108 or a combination thereof. When performed by user device 110, activity monitoring device 104 or continuous glucose monitoring device 102, historical activity logs are retrieved over network 158 if the data is not stored locally. By way of example, analysis module 164, for performing analysis on historical data logs and providing blood glucose response parameters, is part of data logger 108. Analysis module 164 is made up, at least in part, by computer program instructions and their execution by processor 152.

Analysis module 164 is configured to receive historical activity logs and to determine blood glucose response parameters such as blood glucose change parameter, a blood glucose rate of change parameter, and a blood glucose change time delay parameter. Based on product and activity data included in historical activity logs, analysis module 164 is able to determine activity specific and/or product specific blood glucose response parameters. Different users will have a different blood glucose response to consumption of different carbohydrate containing products. Further, users will have a varying blood glucose response to consumption of carbohydrate containing products during different types of activities. Analysis module 164 has access to timestamped activity data, timestamped product data (e.g. when a product of an identified kind has been consumed) and timestamped blood glucose data, thereby allowing analysis module 164 to determine a blood glucose response to varying activities and to consumption of varying carbohydrate containing products. Historical logs include activity data identifying different kinds of activities (e.g. walking, running, cycling), different degrees of strenuousness (e.g. based on heart rate, power, speed, etc. activity metrics) and associated blood glucose data. Such data allows analysis module 164 to predict, for an identified activity and degree of strenuousness, a blood glucose response for the specified user, thereby allowing more accurate predictions on timing and amount of carbohydrate consumption required to keep blood glucose response within a desirable range. Historical activity logs include product data identifying (e.g. based on product identifier 156) varying kinds of carbohydrate containing products having been consumed and the associated blood glucose response. Accordingly, analysis module 164 is able to predict a blood glucose response for a specified user to consumption of a particular carbohydrate containing product. Additionally, analysis module 164 is configured to predict blood glucose response based on an amalgamation of product data, activity data and blood glucose data in historical activity logs. That is, analysis module 164 is configured to analyze historical activity logs and to learn likely blood glucose responses to varying kinds of activity, varying strenuousnesses of activities and consumption of varying carbohydrate containing products during those activities of varying kind and strenuousness.

In accordance with various embodiments, analysis module 164 is configured to determine the blood glucose response parameters based on learnings of plural historical activity logs. For example, user specific blood glucose response parameters can be determined from historical activity logs for the user and an average (or some other calculation) taken from plural such blood glucose response parameters. Such average values can be used to predict when a carbohydrate containing product should be consumed (e.g. based on current activity kind, recent blood glucose values and strenuousness of current activity) and which type of carbohydrate containing product should be consumed (e.g. based on historical blood glucose responses to a plurality of different types of carbohydrate containing product). Accordingly, blood glucose response parameters are useful in determining the product consumption recommendation described herein.

In other embodiments, blood glucose response parameters can be represented in other ways. For example, a continually updated transformation matrix or other operator of blood glucose response parameters can be determined that transforms an input data vector representing a current activity (e.g. activity kind, activity strenuousness, recent blood glucose values, blood glucose trend and any combination thereof) into an output vector including a product consumption recommendation (e.g. including time to consume and type of carbohydrate containing product to consume). The transformation matrix or other operator can embody historical average (or other calculation of historical learnings) blood glucose response parameters as described above. In some embodiments, analysis module 164 is configured as a machine learning algorithm that learns, through training, blood glucose response parameters for a particular user based on historical activity logs. The blood glucose response parameters are embodied in a machine learning algorithm. The machine learning model is configured, after training, to output the product consumption recommendation based on an input vector representing a current activity and current blood glucose values.

In accordance with various embodiments, activity monitoring system 100 is configured to determine, by any one or more processors 118, 124, 140, 152, the product consumption recommendation based on current or recent blood glucose data during a current activity and blood glucose response parameters. In embodiments, the product consumption recommendation includes a recommendation of when the user should consume a carbohydrate containing product and which of plural different carbohydrate containing products the user should consume in order to maintain blood glucose levels within a specified target range during the activity. In some embodiments, activity monitoring device 104 or continuous glucose monitoring device 102, is configured to utilize blood glucose response parameters, provided by analysis module 164, in order to generate the product consumption recommendation as described herein. In some embodiments, analysis module 164 is additionally or alternatively included as part of activity monitoring device 104 or continuous glucose monitoring device 102. Activity monitoring device 104 is configured to display, on display device 114, a notification regarding the product consumption recommendation, as has been described above.

Figure 6:
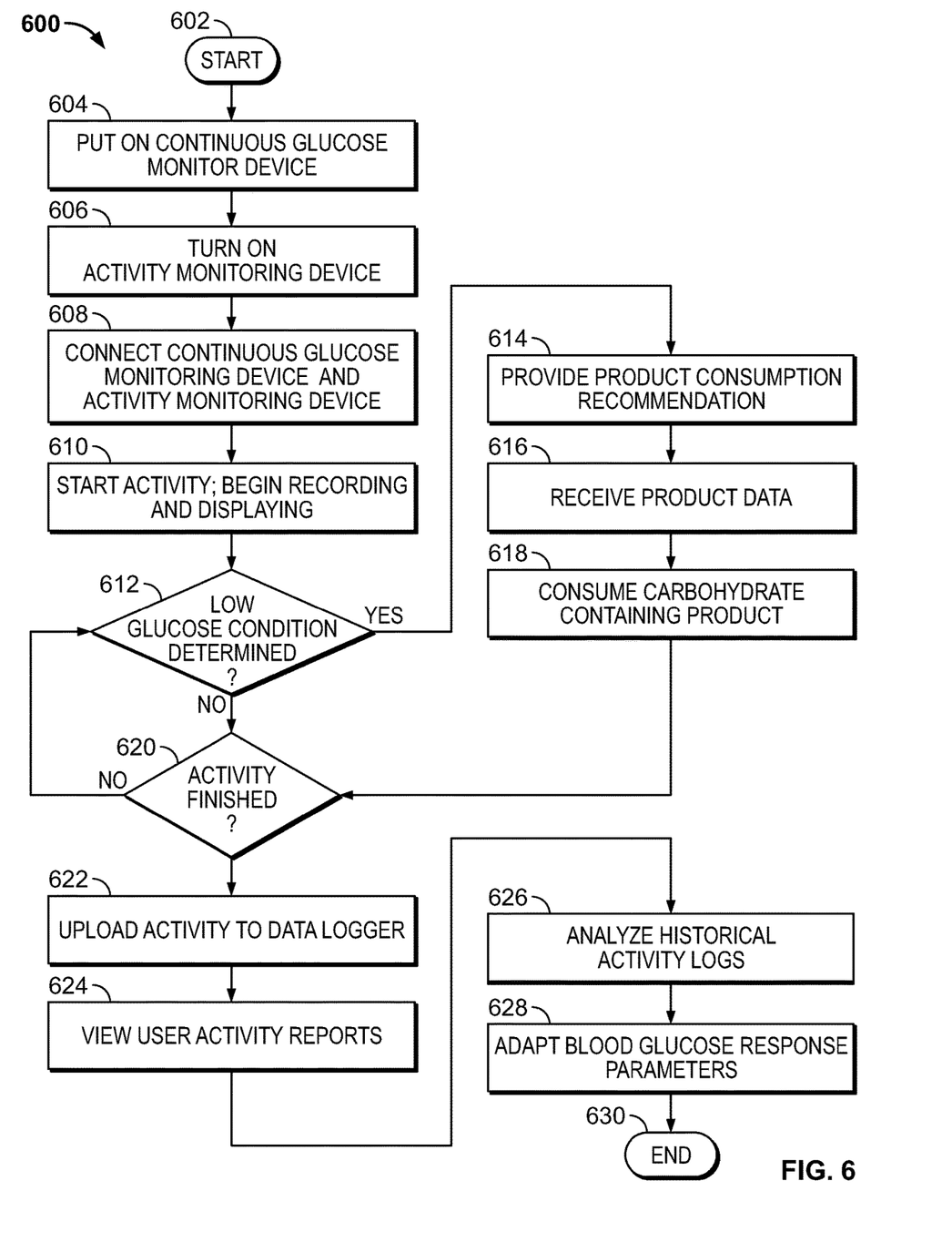
FIG. 6 illustrates a method of activity monitoring, in accordance with various embodiments.

FIG. 6 provides a flowchart representing a method 600 of activity monitoring. The various tasks performed in connection with method 600 may be performed by software, hardware, firmware, or any combination thereof. For illustrative purposes, the following description of method 600 may refer to elements mentioned above in connection with activity monitoring system 100 of FIGS. 1 to 5. In practice, portions of method 600 may be performed by different elements of the described activity monitoring system 100. It should be appreciated that method 600 may include any number of additional or alternative tasks, the tasks shown in FIG. 6 need not be performed in the illustrated order, and method 600 may be incorporated into a more comprehensive procedure or process having additional functionality not described in detail herein. Moreover, one or more of the tasks shown in FIG. 6 could be omitted from an embodiment of the method 600 as long as the intended overall functionality remains intact.

Method 600 starts at 602. In step 604, a user puts on continuous glucose monitor 102. That is, continuous glucose monitor 102 is applied to skin using adhesive patch 200. In doing so, continuous glucose sensor 122 is inserted subcutaneously to be able to sense blood glucose levels of the user. Although continuous glucose monitor 102 is described herein as a subcutaneous device that measures blood glucose levels based on readings taken from interstitial fluid, other types of continuous glucose monitor 102 may be worn by the user such as a non-invasive continuous glucose monitor. Exemplary non-invasive continuous glucose monitoring techniques include near infrared spectroscopy (measuring glucose through the skin using light of slightly longer wavelengths than the visible region), transdermal measurement (attempting to pull glucose through the skin using either chemicals, electricity or ultrasound), measuring the amount that polarized light is rotated by glucose in the front chamber of the eye (containing the aqueous humor), and others.

In step 606, activity monitoring device 104 is turned on or otherwise activated. This step may encompass loading of an activity monitoring app on a smartphone or selecting and starting activity monitoring on a wearable smartwatch using user interface 166. In step 608, continuous glucose monitoring device 102 and activity monitoring device 104 are connected to allow communication of continuous blood glucose data from continuous glucose monitoring device 102 to activity monitoring device 104. In some embodiments, step 608 includes a pairing process whereby wireless communications channel 160 (e.g. Bluetooth channel) is established between continuous glucose monitoring device 102 and activity monitoring device 104 so that activity monitoring device 104 is able to receive continuous blood glucose levels regarding the user.

In step 610, an activity is started. Start of the activity may be automatically sensed by activity monitoring device 104 based on output from activity sensors 116 or a user makes a selection on activity monitoring device when the activity is commenced. A user may select (or automatic detection may be in place) which kind of activity is being started (e.g. walking, running, cycling, swimming, hiking, etc.). After starting the activity, activity monitoring device 104 is configured to receive activity data from activity sensors 116 and cause to be displayed at least some of the activity data on display device 114. As described above with respect to FIG. 4, at least one type of activity metric (e.g. heart rate, speed, distance travelled, calories burned, elevation change, etc.) is displayed through display device 114. Further, activity monitoring device 114 is configured to receive blood glucose data from continuous glucose monitoring device 102. In some embodiments, blood glucose data (e.g. current blood glucose values, blood glucose trend information, information on a target blood glucose range etc.) is displayed through display device 114, e.g. on the same screen as activity data or on a separate screen that can be viewed upon selection by a user using user interface 166. Additionally, activity monitoring device 104 is configured to record activity data and blood glucose data in an activity log during the activity.

In step 612, an existing or predicted low blood glucose condition is determined based on the continuous blood glucose data received from continuous glucose monitoring device 102. Step 612 may be continually assessed as new data is received or intermittently assessed at predetermined time intervals. In embodiments, a low blood glucose condition is determined based on a rate of change of blood glucose data or based on absolute blood glucose values or a combination thereof. In some embodiments, low blood glucose thresholds are dependent on the type of activity being performed. In some embodiments, low blood glucose thresholds are encompassed in user specific blood glucose response parameters determined by analysis module 164 as described herein. In this way, a user specific blood glucose response can be taken into account based on type of activity and strenuousness of activity currently being performed in order to determine low blood glucose thresholds. The low blood glucose threshold(s) represent a lower limit for one or more blood glucose parameters during an activity that indicate when a carbohydrate containing product should be consumed in order to avoid the athlete suffering from hypoglycemia or coming undesirably close to such a low blood glucose condition.

When a low blood glucose condition has been determined in step 612, a product consumption recommendation is determined in step 614. The product consumption recommendation indicates at least when a carbohydrate containing product is to be consumed. Further, based on blood glucose data, the product consumption recommendation may also include which carbohydrate containing product should be consumed from a plurality of different carbohydrate containing products. In one embodiment, rate of change of blood glucose data and absolute values of blood glucose data can be used to predict when one or more low blood glucose thresholds will be passed, thereby indicating when a carbohydrate containing product should be consumed. Further, blood glucose data may be mapped to different carbohydrate containing products (e.g. fast acting or slow acting depending on type of response required), thereby determining which kind of blood glucose data should be consumed. In other embodiments, blood glucose data and optionally also activity data is included as an input vector to analysis module 164. Analysis module 164 uses a machine learning model or other algorithmic technique to determine time and kind of carbohydrate containing product that should be consumed, which takes into account activity metrics (e.g. type of activity, strenuousness of activity) and blood glucose data (e.g. absolute blood glucose values, rate of change of blood glucose) in making the product consumption recommendation. In embodiments, steps 612 and 614 are integrated into a single step as the output from step 614 inherently assesses a low blood glucose condition. However, the pre-assessment of step 612 may allow for processing resources to be conserved.

In accordance with embodiments of the present disclosure, step 614 includes displaying the product consumption recommendation. In embodiments, the product consumption recommendation is provided as a notification 312 (see FIG. 4) that identifies at least when a carbohydrate containing product should be consumed and optionally also which type of carbohydrate containing product should be consumed. In some embodiments, the display of product consumption recommendation is accompanied by a haptic (e.g. vibration) or audible alert.

In step 616, activity monitoring device 104 is provided with product data regarding a product to be consumed. This information can be received via input from user interface 166 of the activity monitoring device 104 or by product reader 106 reading product identifier 156 on packaging of carbohydrate containing product 122. As has been described herein, product reader can operate wirelessly (e.g. by optical scanning or radiofrequency tag reading) to allow product identifier 156 to be read without interrupting the activity. Activity monitoring device 104 is configured to record product data (e.g. product identifier and optionally associated nutritional information) in activity log in association with a timestamp so that a time when a product has been consumed can be recorded.

In step 618, the athlete consumes the carbohydrate containing product responsive to the product consumption recommendation that has been displayed through display device 114 of activity monitoring device 104. Since the user has consumed the carbohydrate containing product 112 at an algorithmically determined time, based on actual blood glucose data and activity data and optionally also user specific blood glucose response parameters, a more systematic approach is being taken to avoid low blood glucose during the activity, thereby reducing the chance of adverse athletic results associated with hypoglycemia.

In step 620, the activity is finished. Completion of an activity can be selected by a user through user interface 166 or automatically determined by activity monitoring device 104 using readings from activity sensors 116. Step 620 includes activity monitoring device 104 completing activity log and storing the activity log in data storage 115. Further, activity monitoring device 104 may cease receiving glucose data from continuous glucose monitoring device 102 and activity data from activity sensors 116. Based on a command from activity monitoring device 104, activity sensor 116 and glucose sensor 122 may be temporarily deactivated (e.g. powered down) in order to conserve battery power.

In step 622, activity log from the completed activity is uploaded to data logger 108. In embodiments, data logger 108 is a cloud-based system and activity log is transmitted thereto over internet-based network 158 from activity monitoring device 104. Activity log may be sent directly from activity monitoring device 104, which has an internet connected wireless interface 120, or activity log may be sent via user device 110. Data logger 108 receives the activity log and stores the activity log along with a historical collection of activity logs in data storage 150 in association with a user profile.

In step 624, a user views one or more activity reports. Activity reports are, in embodiments, hosted by data logger 108 and viewed through display device 162 of user device 110 or display device 114 of activity monitoring device 104. Exemplary activity reports are as shown and described herein with respect to FIG. 5. For example, activity reports may include charts or graphs of glucose data, an activity metric (e.g. heart rate, speed, cadence, energy used, power and/or distance covered) and an indication of consumption of carbohydrate containing products with respect to time.

In step 626, data logger 108 analyzes historical activity logs in data storage 150 to determine adapted blood glucose response parameters (step 628). Analysis of step 626 may be performed after each receipt of a new activity log or upon receipt of a request from continuous glucose monitoring device 102 or activity monitoring device 104. In other embodiments, analysis step 626 and adaptation step 628 are performed by continuous glucose monitoring device 102 or activity monitoring device 104 based on historical activity logs retrieved from data logger 108. As has been described herein, analysis of historical activity logs includes determining blood glucose responses that are specific to a particular activity kind (and optionally strenuousness), to a particular user and to a particular product. That is, historical activity logs include blood glucose data, product data and activity data and thus allow learnings about blood glucose response to activities and carbohydrate product consumption. These learnings are incorporated into blood glucose response parameters (e.g. parameters of a neural network or parameters of a formula to transform input activity and blood glucose data into a product recommendation). The adapted blood glucose response parameters obtained in step 628 are fed back so as to be used when generating a future product consumption recommendation per step 614. Method 600 ends at 630.

Described herein is an activity monitoring system 100 that makes it possible to improve athletic performance through predictive, real-time, low glucose alerts of when a carbohydrate containing product should be consumed. To improve athletic performance during training or competitions, athletes consume carbohydrate containing products such as energy gels, bars, drinks and tablets. Glucose consumption in the body varies based on intensity and duration of exercise, hydration, and other factors. Today, athletes do not know exactly when and how much glucose to consume to achieve optimal performance while exercising. They often rely on the glucose food packaging to determine frequency and quantity of consumption which is often very generic (e.g. "Consume one gel packet every 30 minutes during exercise."). The product consumption recommendations described herein are based on blood glucose data output during the activity from continuous glucose monitoring device 102 with alerts that tell the user when and how much carbohydrate (or what type) to consume to achieve optimal performance. The product consumption recommendation is adaptive depending on user specific blood glucose responses, which have been learned from past activity, product and blood glucose data. That is, the product consumption recommendation generation is user and activity (e.g. swimming, cycling, running, skiing, etc.) specific and takes into account real-time blood glucose data. Activity monitoring system 100 can be used by athletes who are non-diabetic, at risk, pre-diabetic, or type 2 diabetic. In some embodiments, activity monitoring system 100 is not intended for use by type 1 diabetics or athletes requiring insulin to control their condition.

According to the present disclosure, activity monitoring system 100 provides, through display device 114 of activity monitoring device 104, predictive real-time alerts that notify the user before their glucose drops below optimal levels. That is, activity monitoring device 104 may only output a notification (i.e. a product consumption recommendation)

when blood glucose values start to trend downwards and are predicted (using blood glucose response parameters) to go below desirable absolute thresholds or below rate of change thresholds. The continuous glucose monitoring device 102 may be partly re-usable (e.g. a transmitter part) and partly single use (e.g. the blood glucose sensor 122). Alternatively, the blood glucose sensor 122 is also re-usable in separable association with a transmitter part that is for re-use with multiple blood glucose sensors. disposable after the set number of uses. Real-time product consumption recommendations are provided that tell the athlete what carbohydrate containing products to consume, when to consume them, and in what quantity. In some embodiments, a machine learning algorithm improves the alerts and recommendations based on prior product data, activity data and blood glucose data. Product reader 106 provides a wireless communication mechanism with carbohydrate containing products 112 that detects what carbohydrate containing product was consumed and when during an activity.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. An activity monitoring system, comprising:
   a continuous glucose monitoring device for a user, the continuous glucose monitoring device comprising a glucose sensor for monitoring blood glucose levels of the user during an activity;
   an activity monitoring device associable with the user, the activity monitoring device comprising an activity sensor for tracking movement of the user during the activity;
   a display device associable with the user during the activity; and
   at least one processor in operable communication with the continuous glucose monitoring device, the display device and the activity monitoring device, the at least one processor configured to execute program instructions, wherein the program instructions are configurable to cause the at least one processor to:
      receive activity data from the activity monitoring device;
      cause to be displayed at least some of the activity data on the display device;
      receive blood glucose data from the continuous glucose monitoring device;
      determine a product consumption recommendation based on the blood glucose data and the activity data, wherein the product consumption recommendation includes a recommendation of when the user should consume carbohydrates in order to maintain blood glucose levels within a specified target range during the activity; and
      cause to be displayed the product consumption recommendation on the display device.

2. The activity monitoring system of claim 1, wherein the activity sensor includes a Global Positioning System, GPS, receiver.

3. The activity monitoring system of claim 1, wherein the activity sensor includes at least one of an accelerometer and an altimeter.

4. The activity monitoring system of claim 1, wherein the activity data includes at least one of distance, elevation and steps.

5. The activity monitoring system of claim 1, comprising:
   a user interface,
   wherein the program instructions are configurable to cause the at least one processor to:
      receive product data, via the user interface, regarding a carbohydrate containing product; and
      record the activity data, the blood glucose data and the product data with respect to time in an activity log.

6. The activity monitoring system of claim 5, wherein the user interface includes a product reader configured to read data from a package of the carbohydrate containing product.

7. The activity monitoring system of claim 6, wherein the product reader includes at least one of an optical reader and a wireless communications reader.

8. The activity monitoring system of claim 1, wherein the program instructions are configured to cause the at least one processor to determine a downward trend or a low glucose condition in the blood glucose data and to determine the product consumption recommendation based on the downward trend or the low glucose condition in the blood glucose data.

9. The activity monitoring system of claim 1, wherein the program instructions are configured to cause the at least one processor to determine the product consumption recommendation based on the blood glucose data, wherein the product consumption recommendation includes a recommendation of when the user should consume a carbohydrate containing product and which carbohydrate containing product, from a plurality of carbohydrate containing products, the user should consume in order to maintain desirable blood glucose levels within a specified target range during the activity.

10. The activity monitoring system of claim 1, wherein the program instructions are configured to cause the at least one processor to analyze historical activity logs including historic activity data, blood glucose data and product data with respect to time in order to generate one or more blood glucose response parameters, wherein the one or more blood glucose response parameters represent the user's blood glucose response to consuming one or more carbohydrate containing products, and wherein the program instructions are configured to cause the at least one processor to determine the product consumption recommendation based on current glucose data, current activity data and the one or more blood glucose response parameters.

11. The activity monitoring system of claim 10, wherein the one or more blood glucose response parameters include at least one of a blood glucose change parameter, a blood glucose rate of change parameter, and a blood glucose change time delay parameter.

12. The activity monitoring system of claim 1, wherein the activity monitoring device is a wearable device or a smart phone paired with the continuous glucose monitoring device.

13. The activity monitoring system of claim 1, wherein the glucose sensor includes a sensor electrode for subcutaneous placement.

14. The activity monitoring system of claim 1, wherein the program instructions are configured to cause the at least one processor to use a machine learning algorithm to determine a time to consume a carbohydrate containing product and a kind of carbohydrate containing product as part of the product consumption recommendation, wherein the machine learning algorithm receives activity metrics included in the activity data and blood glucose data as inputs.

15. The activity monitoring system of claim 14, wherein the program instructions are configured to cause the at least one processor to cause the machine learning algorithm to learn blood glucose response parameters for a particular user based on historical activity logs such that the machine learning algorithm is configured, after training, to output the product consumption recommendation based on an input vector representing a current activity and current blood glucose values, wherein the historical activity logs include historic activity data, the blood glucose data and product data with respect to time.

16. A method of monitoring an activity, the method comprising:
 receiving, by at least one processor, activity data from an activity monitoring device for tracking movement of a user during an activity;
 displaying, by the at least one processor, at least some of the activity data on a display device associated with the user during the activity;
 receiving, by the at least one processor, blood glucose data from a continuous glucose monitoring device worn by the user during the activity;
 determining, by the at least one processor, a product consumption recommendation based on the blood glucose data, wherein the product consumption recommendation includes a recommendation of when the user should consume a carbohydrate containing product in order to maintain blood glucose levels within a specified target range during the activity; and
 displaying, by the at least one processor, the product consumption recommendation on the display device during the activity.

17. The method of claim 16, comprising:
 reading product data from a package of a carbohydrate containing product during the activity using an optical reader or a wireless communications reader;
 receiving, by the at least one processor, the product data; and
 recording, by the at least one processor, the activity data, the blood glucose data and the product data in an activity log with respect to time.

18. The method of claim 16, comprising:
 analyzing one or more historical activity logs including activity data, blood glucose data and product data using a machine learning algorithm to determine user response parameters, wherein the user response parameters represent a user's blood glucose response to consuming different carbohydrate containing products during a given activity.

19. The method of claim 18, comprising:
 determining, by the at least one processor, the product consumption recommendation based on the blood glucose data and the user's blood glucose response, wherein the product consumption recommendation includes a recommendation of when the user should consume a carbohydrate containing product and which of the different carbohydrate containing products the user should consume in order to maintain blood glucose levels within a specified target range during the activity.

20. A non-transitory computer-readable storage medium having program instructions, for monitoring an activity, wherein the program instructions are configurable to cause at least one processor to:
 receive activity data from an activity monitoring device associated with a user during an activity;
 displaying at least some of the activity data on a display device associated with the user during the activity;
 receive blood glucose data from a continuous glucose monitoring device worn by the user during the activity;
 determine a product consumption recommendation based on the blood glucose data, wherein the product consumption recommendation includes a recommendation of when the user should consume a carbohydrate containing product and a quantity of carbohydrate containing product that the user should consume in order to maintain blood glucose levels within a specified target range during the activity; and
 display the product consumption recommendation on the display device during the activity.

* * * * *